(12) United States Patent
Kambe et al.

(10) Patent No.: US 7,547,537 B2
(45) Date of Patent: Jun. 16, 2009

(54) URETHANE-BOND-DEGRADING BACTERIA

(75) Inventors: Toshiaki Kambe, Tsukuba (JP); Yukie Shigeno, Tsukuba (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 296 days.

(21) Appl. No.: 10/538,014

(22) PCT Filed: Mar. 3, 2004

(86) PCT No.: PCT/JP2004/002691

§ 371 (c)(1),
(2), (4) Date: Jun. 7, 2005

(87) PCT Pub. No.: WO2004/078952

PCT Pub. Date: Sep. 16, 2004

(65) Prior Publication Data

US 2007/0099285 A1    May 3, 2007

(30) Foreign Application Priority Data

Mar. 3, 2003  (JP)  ............................ 2003-055421

(51) Int. Cl.
   *C12N 1/20*  (2006.01)
(52) U.S. Cl. ............................. 435/252.1; 435/252.32
(58) Field of Classification Search ............... None
   See application file for complete search history.

(56) References Cited

U.S. PATENT DOCUMENTS 6,040,154 A    3/2000    Fayolle et al.

FOREIGN PATENT DOCUMENTS

JP    9-192633 A    7/1997

OTHER PUBLICATIONS

Ohshiro et al., Appl Microbiol Biotechnol (1997) 48: 546-548p.*
http://www.atcc.org/common/catalog/wordSearch/results.cfm, accessed Nov. 6, 2007.*
Yusuke Adachi et al., Japan Society for Bioscience, Biotechnology, and Agrochemistry 2003 Nendo (Heisei 15 Nendo) Taikai Koen Yoshoshu, Mar. 5, 2003, p. 234.
Yukie Shigeno (Akutsu) et al., Bioscience & Industry, Mar. 11, 2002, vol. 60, No. 3, pp. 153 to 158.
Nakajima-Kambe T. et al., FEMS Microbiol. Lett. 1995, vol. 195, pp. 39 to 42.
Jansen B. et al., Zentralbl. Bakterial. 1991, vol. 276, No. 1, pp. 36 to 45.
M. J. Kay et al.; International Biodeterioration, 27, pp. 205-222, 1991.
M. J. Kay et al.; International Biodeterioration & Biodegradation, 31, pp. 209-225, 1993.
T. Nakajima-Kambe et al.; Applied Microbiology and Biotechnology, vol. 51, No. 2, pp. 134-140, Feb. 1999.
G.T. Howard et al.; Letters in Applied Microbiology, vol. 32, No. 3, pp. 211-214, Mar. 2001.
Gary T. Howard; International Biodeterioration & Biodegradation; vol. 49, pp. 245-252, 2002.
Yukie Akutsu-Shigeno et al.; Applied Microbiology and Biotechnology, vol. 70, No. 4, pp. 422-429, 2006.
Istvan Nagy et al.; Journal of Bacteriology, vol. 177, No. 3, pp. 676-687, Feb. 1995.
Yukie Akutsu et al., Applied and Environmental Microbiology, Jan. 1998, pp. 62-67, vol. 64, No. 1.
Yukie Shigeno-Akutsu et al., Journal of Bioscience and Bioengineering, vol. 88, No. 5, pp. 484-487, 1999.

* cited by examiner

*Primary Examiner*—Irene Marx
(74) *Attorney, Agent, or Firm*—Birch, Stewart, Kolasch & Birch, LLP (57) ABSTRACT

Microbial biodegradation can be presented as a preferred technique for plastic disposal from the viewpoint of protection of the natural environment, but a problem exists in that plastics are generally not biodegradable. The present invention provides a microorganism capable of degrading a urethane compound and a method for degrading a urethane compound using the microorganism. More particularly, the present invention aims to provide a microorganism capable of degrading a urethane compound used as a source material for polyurethanes and a method for degrading a polyurethane using the microorganism.

2 Claims, 5 Drawing Sheets

URETHANE-BOND-DEGRADING BACTERIA

TECHNICAL FIELD

The present invention relates to a novel microorganism and a method for degrading polyurethanes through biological treatment using the microorganism.

BACKGROUND ART

In recent years, plastic waste disposal has become a problem. Procedures mainly used for plastic waste disposal are incineration and reclamation. However, incineration is disadvantageous in that it accelerates global warming, while reclamation suffers from problems such as lack of landfills for reclamation. For example, polyurethanes are consumed all over the world at a rate of about 6,000,000 tons per year and in Japan at a rate of about 550,000 tons per year. Among them, foam cushioning materials made of polyurethanes are used on a massive scale as heat insulators, e.g., for refrigerators because of their excellent heat insulation properties. At present, polyurethane waste is often disposed of in landfills as noncombustible garbage, but problems are associated with its disposal, such as lack of landfills, and environmental pollution. While microbial biodegradation can be presented as a preferred disposal technique from the viewpoint of protection of the natural environment, a problem exists in that polyurethanes are not biodegradable.

Polyurethane contains urethane bonds together with ester or ether bonds in its molecule, and degradation proceeds through cleavage of these bonds. There are some reports of ester bonds in polyol units being cleaved by fungi and/or bacteria. Darby et al. (Darby R. T. and Kaplan A. M., Fungal susceptibility of polyurethanes. Appl. Microbiol., 16, 900-905 (1968)) have performed fungal degradation tests on various polyurethanes. They have reported that ester-based polyurethanes are more sensitive to degradation than ether-based polyurethanes, and that degradation profiles vary depending on the type of isocyanate and/or polyol. Kay et al. (Kay, M. J., McCabe, R. W., Morton, L.H.G., Chemical and physical changes occurring in polyester polyurethane during biodegradation. Int. Biodeterio. Biodegrad., 31, 209-225 (1991)) have isolated 15 bacterial strains capable of degrading ester-based polyurethanes and have also reported the results of degradation profiles examined for Corynebacterium strains having a strong degradation ability.

However, there is almost no knowledge or information about degradation of urethane bonds in polyurethanes. Although some reports indicate that urethane bonds are hydrolyzed during microbial degradation, no clear causal relation has been found between urethane bond cleavage and microorganisms (B. Jansen et al., Evidence for degradation of synthetic polyurethanes by *Staphylococcus epidermidis*. Zentralbl Bakteriol., 276, 36 (1991); Darby R. T. and Kaplan A. M., Fungal susceptibility of polyurethanes. Appl. Microbiol., 16, 900-905 (1968)).

On the other hand, low molecular urethane compounds are already reported to undergo microbial degradation, and such degradation is known to be catalyzed by esterase. However, most of these reports are directed to improvement of alcohol drinks or degradation/clarification of carbamate insecticides (JP 01-300892 A, JP 01-240179 A, JP 02-128689 A, JP 03-175985 A, JP 04-104784 A, JP 04-325079 A); none of these techniques can be adapted to polyurethane degradation. Fungal degradation is reported as a technique for degrading substances which can be used as source materials for polyurethanes (JP 09-192633 A), but this technique does not use bacteria that can be easily adapted for large scale culture.

In relation to solid polyurethane-degrading bacteria, the following strains are known to degrade polyester-based polyurethanes: *Paenibacillus amylolyticus* strain TB-13 (Japanese Patent Application No. 2002-334162) and *Comamonas acidovorans* strain TB-35 (T. Nakajima-Kambe, F. Onuma, N. Kimpara and T. Nakahara, Isolation and characterization of a bacterium which utilizes polyester polyurethane as a sole carbon and nitrogen source. FEMS Microbiology Letters, Vol. 129, 39-42, 1995). However, while these strains do actually degrade ester bonds in urethane, they do not substantially degrade urethane bonds. Thus, to ensure complete bacterial degradation of polyurethanes, there is a demand for bacteria that are capable of degrading urethane bonds.

DISCLOSURE OF THE INVENTION

The object of the present invention is to provide a novel microorganism capable of degrading a urethane compound and a method for degrading a urethane compound using the microorganism. More particularly, the present invention aims to provide a microorganism capable of degrading a urethane compound used as a source material for polyurethanes and a method for degrading a polyurethane using the microorganism.

To achieve the object stated above, the inventors of the present invention have screened microorganisms which degrade low-molecular-weight urethane compounds used as source materials for polyurethane synthesis and have found that microorganisms belonging to the genus *Rhodococcus* have the ability to degrade urethane compounds. It should be noted that microorganisms belonging to the genus *Rhodococcus* were not previously known to have any ability to degrade urethane compounds. The inventors of the present invention have also found a method for degrading a polyurethane using a microorganism belonging to the genus *Rhodococcus*.

Namely, the present invention provides a microorganism belonging to the genus *Rhodococcus* and having the ability to degrade a urethane compound, particularly a low-molecular-weight urethane compound used as a source material for polyurethane synthesis, as well as providing a method for degrading a polyurethane using the microorganism belonging to the genus *Rhodococcus*.

DETAILED DESCRIPTION OF THE INVENTION

As stated above, the present invention provides a microorganism belonging to the genus *Rhodococcus* and having the ability to degrade a urethane compound, particularly a low-molecular-weight urethane compound used as a source material for polyurethane synthesis, as well as providing a method for degrading a polyurethane using the microorganism belonging to the genus *Rhodococcus*.

Microorganisms belonging to the genus *Rhodococcus* and having the ability to degrade a urethane compound may be either known or newly screened microorganisms. By way of example, screening of microorganisms may be accomplished as follows. Soil samples collected from various areas are introduced into test tubes containing a medium supplemented with a low-molecular-weight urethane compound used as a source material for polyurethane synthesis, followed by shaking culture at 30° C. After repeating subculture every one week, those samples showing cloudiness or discoloration in the culture solutions are selected and their culture supernatants are diluted and applied onto NB agar plates, followed by culturing at 30° C. for 1 to 3 days. The grown colonies are picked up and defined as candidate strains for urethane-bond-degrading bacteria. The resulting candidate strains are then cultured in a liquid medium containing, as a carbon source, a low-molecular-weight urethane compound (urethane compound I) which is obtained through reaction between toluene diisocyanate and butanol, followed by selection of strains showing the production of toluenediamine (a urethane bond hydrolysis product of urethane compound I) in their culture solutions.

The microorganism of the present invention is not limited in any way as long as it belongs to the genus *Rhodococcus* and has the ability to degrade a urethane bond-containing compound. More specifically, typical examples include *Rhodococcus equi* TB-60-DSMZ 16175 internationally deposited on Jan. 24, 2004 with the German depositary institution DSMZ [Deutsche Sammlung von Mikroorganismen und Zellkulturen GmbH (German Collection of Microorganisms and Cell Cultures), Mascheroder Weg 1 B, D-38124 Braunschweig, Germany], which is *Rhodococcus equi* strain TB-60 that was not accepted although an application for deposit was filed on Feb. 26, 2003 with the International Patent Organism Depositary, the National Institute of Advanced Industrial Science and Technology in Japan. Mycological properties of *Rhodococcus* strains can be found in BERGEY'S MANUAL OF Systematic Bacteriology (vol. 1, 1984, vol. 2, 1986, vol. 3, 1989, vol. 4, 1989).

Moreover, the microorganism of the present invention may be either a wild-type or mutant strain as long as it is a *Rhodococcus* strain having the ability to degrade urethane bonds.

Mutant strains may be obtained by mutagenesis with ethylmethanesulfonic acid (a conventionally commonly used mutagen), treatment with other chemical substances (e.g., nitrosoguanidine, methylmethanesulfonic acid), ultraviolet irradiation, or so-called spontaneous mutation without using any mutagen.

Any medium can be used without particular limitation in culturing microorganisms belonging to the genus *Rhodococcus* as long as it allows growth of microorganisms belonging to the genus *Rhodococcus*. Examples include, but are not limited to, LB medium (1% tryptone, 0.5% yeast extract, 1% NaCl). More specifically, the medium used for growing the microorganism of the present invention may contain a carbon source (e.g., glucose) assimilable by the microorganism of the present invention and a nitrogen source assimilable by the microorganism of the present invention. Such a nitrogen source includes an organic nitrogen source such as peptone, meat extract, yeast extract or corn steep liquor, as well as an inorganic nitrogen source such as ammonium sulfate or ammonium chloride. If desired, the medium may further contain salts composed of cations (e.g., sodium ion, potassium ion, calcium ion, magnesium ion) and anions (e.g., sulfate ion, chlorine ion, phosphate ion). Moreover, the medium may also be supplemented with trace components such as vitamins and nucleic acids. The concentration of a carbon source ranges from, e.g., around 0.1% to 10%, while the concentration of a nitrogen source will vary depending on its type, but ranges from, e.g., around 0.01% to 5%. The concentration of an inorganic salt ranges from, e.g., around 0.001% to 1%.

The urethane compound which can be degraded in the present invention is not limited in any way as long as it has urethane bonds in its molecular structure. Non-limiting examples include toluene-2,4-carbamic acid dibutyl ester, toluene-2,6-dicarbamic acid dibutyl ester, methylenebisphenyldicarbamic acid dibutyl ester, hexamethylene-dicarbamic acid dibutyl ester, norbornenedicarbamic acid dibutyl ester, as well as polyurethanes synthesized from these materials.

The term "polyurethane" is a generic name for high molecular compounds having urethane bonds (—NH-COO—) in their molecule and it means a polymer having groups such as ester, ether, amide, urea and/or carbamate, which is obtained by reaction between a multifunctional isocyanate and a hydroxyl group-containing compound. When varying the functionality of hydroxyl or isocyanate groups, it is possible to prepare a wide variety of branched or crosslinked polymers. They can be broadly divided into ester-based and ether-based polyurethanes based on the type of polyol being used. Because of their good properties such as easy processability, resistance to putrefaction, resistance to spoilage and low density, polyurethanes have a wide range of uses including elastic materials, foamed materials, adhesives, coating materials, fibers and synthetic leather, and are also widely used as automobile components. There is no particular limitation on the number average molecular weight of polyurethane resins which can be treated by the degradation method of the present invention.

Further, the present invention provides a method for degrading a urethane bond-containing compound by the action of microorganisms. This method is based on a phenomenon that urethane bonds are degraded and consumed as a nutrient source during growth of microorganisms, or on the action of microbial enzymes to degrade urethane bonds, i.e., on the use of grown microorganism cells such as resting cells. Alternatively, before being provided for treatment of urethane compounds, these cells may be lyophilized in a routine manner to give a cell powder, and may further be blended with various vitamins, minerals and necessary nutrient sources (e.g., yeast extract, casamino acid, peptone) for formulation into solid preparations including tablets. Likewise, strains per se may also be used as components of activated sludge and compost.

Urethane compounds to be degraded may be added in emulsion or powder form to a liquid medium or may be added in massive form such as films or pellets. It should be noted that the amount of urethane compounds added to the medium is desirably 0.01% to 10% by weight. Microorganisms may be added in a very small amount; and it is preferable to use them in an amount of 0.1% by weight or more (wet weight) relative to urethane compounds in consideration of degradation efficiency. Urethane compounds to be degraded may be provided either alone or in combination.

In an embodiment based on a phenomenon in which urethane bonds are degraded and consumed as a nutrient source during growth of microorganisms, urethane compounds may be provided as a sole carbon source or as a sole carbon and nitrogen source, or together with other carbon and/or nitrogen sources. The medium available for use may contain a urethane compound(s) or glucose or the like as a carbon source, as well as a nitrogen source assimilable by the microorganism of the present invention, including an organic nitrogen source (e.g., peptone, meat extract, yeast extract, corn steep liquor) or an inorganic nitrogen source (e.g., ammonium sulfate, ammonium chloride). If desired, the medium may further contain salts composed of cations (e.g., sodium ion, potassium ion, calcium ion, magnesium ion) and anions (e.g., sulfate ion, chlorine ion, phosphate ion). Moreover, the medium may also be supplemented with trace components such as vitamins and nucleic acids. The concentration of a carbon source ranges from, e.g., around 0.1% to 10%, while the concentration of a nitrogen source will vary depending on its type, but ranges from, e.g., around 0.01% to 5%. The concentration of an inorganic salt ranges from, e.g., around 0.001% to 1%.

In an embodiment using the action of microbial enzymes to degrade urethane bonds, i.e., in an embodiment using grown microorganism cells such as resting cells, since there is no need to grow the microorganisms during degradation of urethane bonds, the medium may be a buffer containing a urethane compound(s), which may further be supplemented with nitrogen sources, inorganic salts, vitamins, etc. Examples of a buffer include phosphate buffer.

The time required for degradation of urethane compounds will vary depending on the type, composition, shape and amount of urethane compounds to be degraded, the type and amount (relative to urethane compounds) of microorganisms used, as well as various culture conditions, etc.

In the present invention, the degradation of urethane compounds can be observed when static culture, shaking culture or aeration culture is performed on the above microorganisms under aerobic conditions. Preferred is rotary shaking culture, a rotation speed of which may be in the range of 30 to 250 rotations per minute. In relation to culture conditions, the culture temperature may be 10° C. to 50° C., particularly preferably around 30° C. The pH of the medium may be in the range of 4 to 10, preferably around 7.

Degradation of urethane compounds in the medium can be confirmed, e.g., by measuring the weight loss of urethane compounds provided for degradation, by measuring the amount of residual urethane compounds by high performance liquid chromatography (HPLC), or by measuring the generation of diamine compounds (urethane bond hydrolysis products). The generation of diamine compounds can be confirmed, e.g., by thin-layer chromatography using, as standard substances, diamine compounds expected to be generated, or by gas chromatography.

In an embodiment of a method for degrading a solid polyurethane, complete degradation of the polyurethane can be achieved by using *Paenibacillus amylolyticus* strain TB-13 (Accession No. FERM P-19104, see Japanese Patent Application No. 2002-334162) and/or *Comamonas acidovorans* strain TB-35, both of which are known to degrade ester bonds in polyester-based polyurethanes, in combination with the microorganism of the present invention having the ability to degrade urethane bonds.

EXAMPLES

The present invention will now be further described in more detail by way of the following examples, which are not intended to limit the scope of the invention.

Example 1

Figure 1:
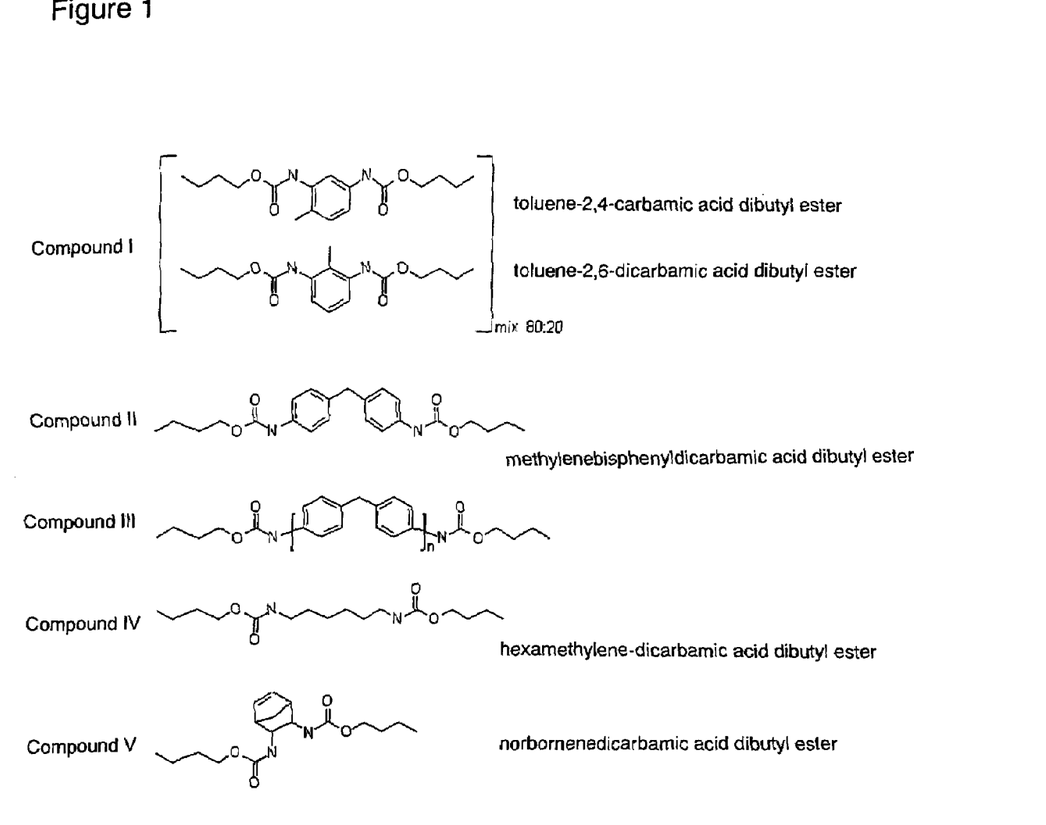
FIG. 1 shows the structure of synthetic urethane compounds used for screening of urethane-bond-degrading bacteria.

Screening of Urethane-bond-degrading Bacteria
Synthesis procedures for urethane compounds Synthesized urethane compounds (FIG. 1) were used for screening of urethane-bond-degrading bacteria. These compounds were urethanized products prepared by reacting butanol with five typical isocyanates used as industrial source materials for polyurethanes, including toluene diisocyanate (TDI), methylenebisphenyl diisocyanate (MDI), hexamethylene diisocyanate (HDI) and norbornene diisocyanate (NBDI). These compounds (urethane compounds I to V, see FIG. 1) were each a substance having urethane bonds in its molecule, which was solid at atmospheric temperature and insoluble in water.

Medium

The screening medium used for screening of urethane-bond-degrading bacteria was prepared as follows. The inorganic salt medium shown in Table 1 was dispensed in 10 ml volumes into large test tubes with an inner diameter of 22 mm and then supplemented with urethane compounds I to V (about 0.1 g), respectively, as a carbon source, followed by sterilization at 121° C. for 20 minutes. All reagents used for medium preparation were of reagent grade or equivalent quality, commercially available from Wako Pure Chemical Industries, Ltd., Japan.

TABLE 1

| Medium for screening | |
|---|---|
| Composition | g/l |
| $KH_2PO_4$ | 0.6 |
| $K_2HPO_4$ | 1.6 |
| $NH_4NO_3$ | 1.0 |
| $MgSO_4 7H_2O$ | 0.2 |
| $CaCl_2 2H_2O$ | 0.01 |
| $FeCl_3 6H_2O$ | 0.01 |
| $ZnSO_4 7H_2O$ | 0.01 |
| $MnSO_4 4H_2O$ | 0.01 |
| Vitamin mixture | |
| | PH 7.0 |

| **Vitamin mixture Composition | Final concentration mg/l |
|---|---|
| Nicotinamide | 10 |
| Ca pantothenate | 2.5 |
| Thiamine HCl | 2.5 |
| Riboflavin | 1.25 |
| Pyridoxine | 0.75 |
| p-Aminobenzoate | 0.6 |
| Folic acid | 0.5 |
| Biotin | 0.1 |

Screening

Soil samples (350 samples) collected from various areas of Japan were used as screening sources. Fifty test tubes were used for each of urethane compounds I to V (250 tubes in total). These soil samples were mixed together in groups of 20 samples and added in an amount of 0.2 g per 10 test tube containing the above screening medium. Each test tube was cultured with shaking at 30° C. at 125 osc/min and the supernatant (0.5 ml) from each tube was transferred to fresh screening medium every one week. After repeating this procedure three times, 26 test tube samples showing cloudiness or discoloration in the culture solutions were selected and their culture supernatants were diluted with physiological saline and applied onto NB agar plates, followed by culturing at 30° C. for 1 to 3 days. The grown colonies were picked up on a one-by-one basis and used as candidate strains for urethane-bond-degrading bacteria. After culturing on NB agar plates at 30° C., the bacterial cells were suspended in a 20% glycerol solution and stored at −80° C.

The candidate strains thus obtained were cultured at 30° C. at 125 osc/min in a liquid screening medium containing urethane compound I as a carbon source, and were then confirmed for the generation of toluenediamine (a urethane bond hydrolysis product of urethane compound I) in their culture solutions by thin-layer chromatography. Each culture supernatant (0.5 ml) was extracted with an equal volume of ethyl acetate and the resulting ethyl acetate layer (60 µl) was spotted onto a thin layer plate (Merck, Kieselgel 60$F_{254}$). A 80:35:3 mixture of ethyl acetate, methanol and water was used as a developing solvent. As a standard substance, toluenediamine was also spotted and used for confirmation of Rf values, with black spots being produced due to absorption under UV irradiation. As a result, one strain was obtained which showed the production of toluenediamine, a urethane bond hydrolysis product. This strain was defined as the strain TB-60 and stored at −80° C. It should be noted that this strain was obtained from the screening system using compound I.

Example 2

Identification of Urethane-bond-degrading Strain TB-60

Physiological tests were performed according to standard procedures. Identification was accomplished by referring to Bergey's Manual of Systematic Bacteriology, Baltimore: WILLIAMS & WILKINS Co., (1984), along with using a microorganism identification system (Microlog 3, BIOLOG, USA). Sequencing and analysis of 16srDNA were conducted by direct PCR using a primer set of 27F and 1492R capable of amplifying almost the full-length of eubacterial 16SrDNA.

Morphological and Physiological Property Test

Table 2 shows the results of the strain TB-60 tested for various morphological and physiological properties. This strain was a Gram-positive coryneform bacterium and showed neither motility nor sporulation. Moreover, this strain formed a white semi-liquid colony extremely rich in water. This strain was negative in the oxidase test, positive in the catalase test, and negative in the OF test.

TABLE 2

Mycological properties of urethane-degrading strain TB-60

| Morphological properties | |
| --- | --- |
| Morphology | coryneform |
| Gram stain | positive |
| Sporulation | no |
| Motility | no |
| Colony morphology | white, semitransparent, semi-liquid, indefinite shape, diffusible |
| Physiological properties | |
| Behavior for oxygen | aerobic |
| Cytochrome oxidase activity | negative |
| Catalase activity | positive |
| O-F test | negative |

Identification with a BIOLOG Identification System

As a result of the identification test using a BIOLOG bacterial identification system, this strain was identified as *Rhodococcus equi* with 95% probability. No other strains were found to have 50% or more similarity.

TABLE 3

Identification results of strain TB-60 by BIOLOG

| | Possibility (%) |
| --- | --- |
| *Rhodococcus equi* | 95 |
| *Corynebacterium hoagii* | 4 |
| *Brevibacterium mcbrellneri* | 0 |
| *Corynebacterium lipophiloflavum* | 0 |
| *Corynebacterium jeikeium* | 0 |

16SrDNA Nucleotide Sequence

Almost the full-length of 16SrDNA was amplified from this strain by colony direct PCR and sequenced for an upstream region of 535 bp (SEQ ID NO: 1) and a downstream region of 497 bp (SEQ ID NO: 2).

Figure 2:
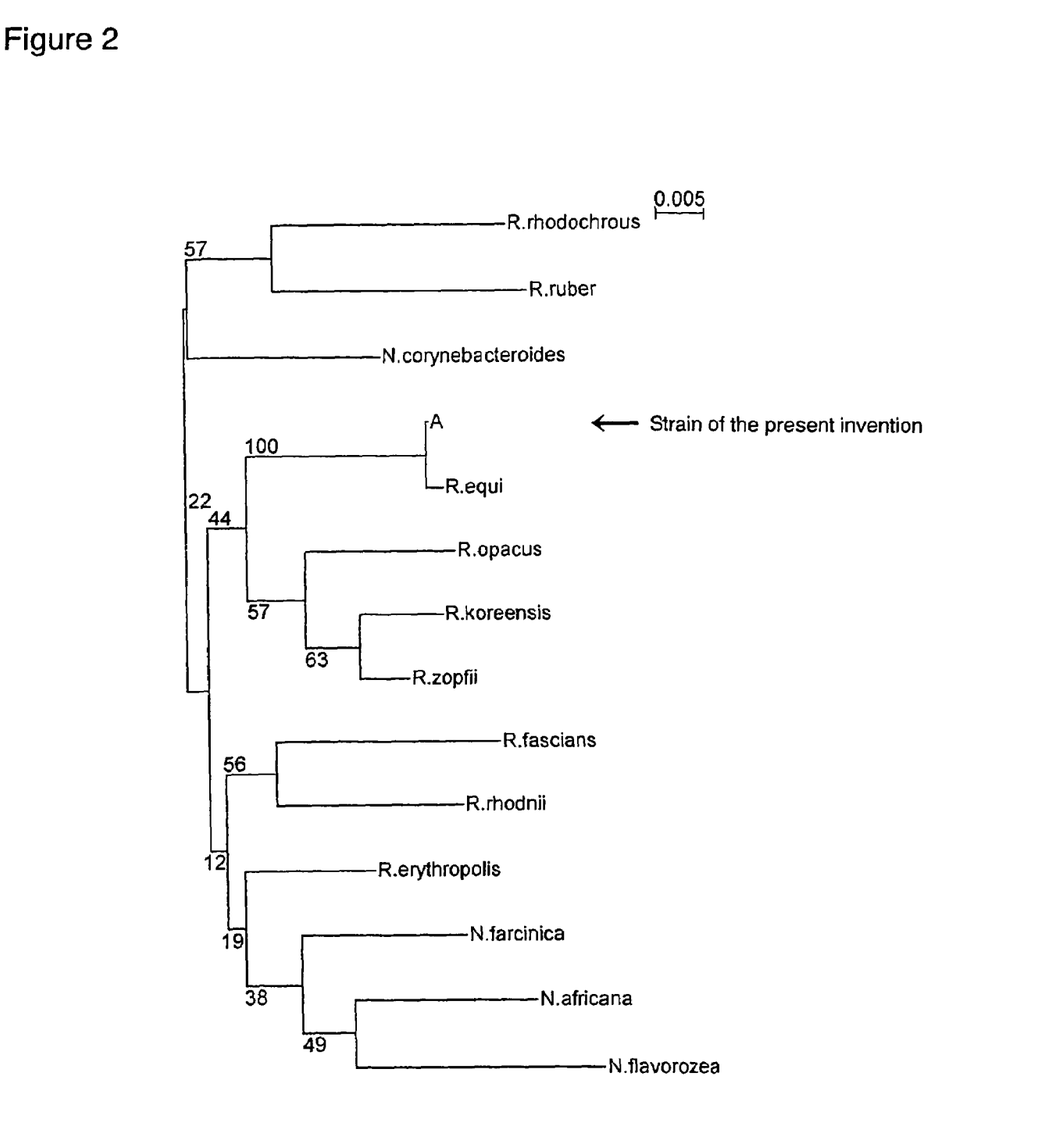
FIG. 2 shows an rDNA sequence-based dendrogram including known strains.

When a BLAST homology search was performed based on the resulting sequences, this strain was recognized as *Rhodococcus equi* with a 98% match in the upstream region and a 100% match in the downstream region. FIG. 2 shows a sequence-based dendrogram including known strains.

These results identified this strain as *Rhodococcus equi*.

Example 3

Degradation Test on Urethane Compounds Using *Rhodococcus egui* Strain TB-60

Test strain

*Rhodococcus equi* strain TB-60 was used, which was obtained as a urethane compound-degrading bacterium.

Medium and Reagents

In addition to the above-mentioned screening medium, a medium containing the same ingredients except for the nitrogen source was used in the experiment to culture the strain in the presence of urethane compound I as a carbon source or as a carbon/nitrogen source. All reagents used in the experiment were of reagent grade or equivalent quality, commercially available from Wako Pure Chemical Industries, Ltd., Japan.

Culture Conditions

Urethane compound I dissolved at 2% in diethyl ether was dispensed in 0.1 ml volumes into small test tubes with an inner diameter of 16 mm, allowed to stand in a draft chamber to sufficiently volatilize diethyl ether and then, after addition of 2 ml medium, was sterilized in an autoclave at 120° C. for 20 minutes. *Rhodococcus equi* strain TB-60 was suspended in sterilized physiological saline at $O.D._{660}$ =0.2 and inoculated in 100 µl volumes into each test tube, followed by rotary shaking culture at 30° C. at 300 rpm for 0 to 10 days. The experiment was performed in triplicate for each case using uninoculated tubes as a control.

Measurement of the Amount of Bacterial Cells Grown

The amount of bacterial cells grown was determined by measuring the culture solutions for their $O.D._{660}$ with an absorptiometer. The absorbance was measured using an absorptiometer V-550 (JASCO Engineering Co. Ltd., Japan).

Measurement of the Degree of Urethane Degradation

The amount of residual urethane compound I was measured by high performance liquid chromatography (HPLC). After addition of 2 ml acetonitrile, each culture solution was stirred well and allowed to stand for 20 minutes. The supernatant was transferred to a microtube and centrifuged at 12,000 rpm at 4° C. The resulting supernatant was further transferred to a 2 ml vial and provided as a sample for HPLC in a volume of 10 μl. The column used was a TSK-GEL ODS-80TM (4.6 mm×15 cm, Tosoh Corporation, Japan) and the analysis was performed using 70% acetonitrile as a mobile phase at a flow rate of 0.6 ml/min. A UV detector (240 nm) was used as a detector.

Measurement of the Amount of Diamine Generated

The amount of toluenediamine generated in response to the degradation of urethane bonds was quantified by gas chromatography (GC). After completion of the culturing, each culture supernatant (0.5 ml) was transferred to a microtube, supplemented with an ethyl acetate solution (0.5 ml) containing 100 ppm diphenylamine as an internal standard substance, and then stirred well for 10 minutes. After centrifugation at 12,000 rpm at 4° C., the upper layer was transferred to a new microtube, dehydrated with anhydrous sodium sulfate (about 80 mg) and provided as a sample for GC in a volume of 2 μl. The GC analysis was performed with GC-2010 (Shimadzu Corporation, Japan) and diphenylamine was used as an internal standard for concentration calculation. The column used was a DB-1 (0.25 mm×30 m, J & W). The column temperature was set to 180° C. and the injector temperature was set to 300° C. An FID detector was used for detection.

Results

Figure 3:
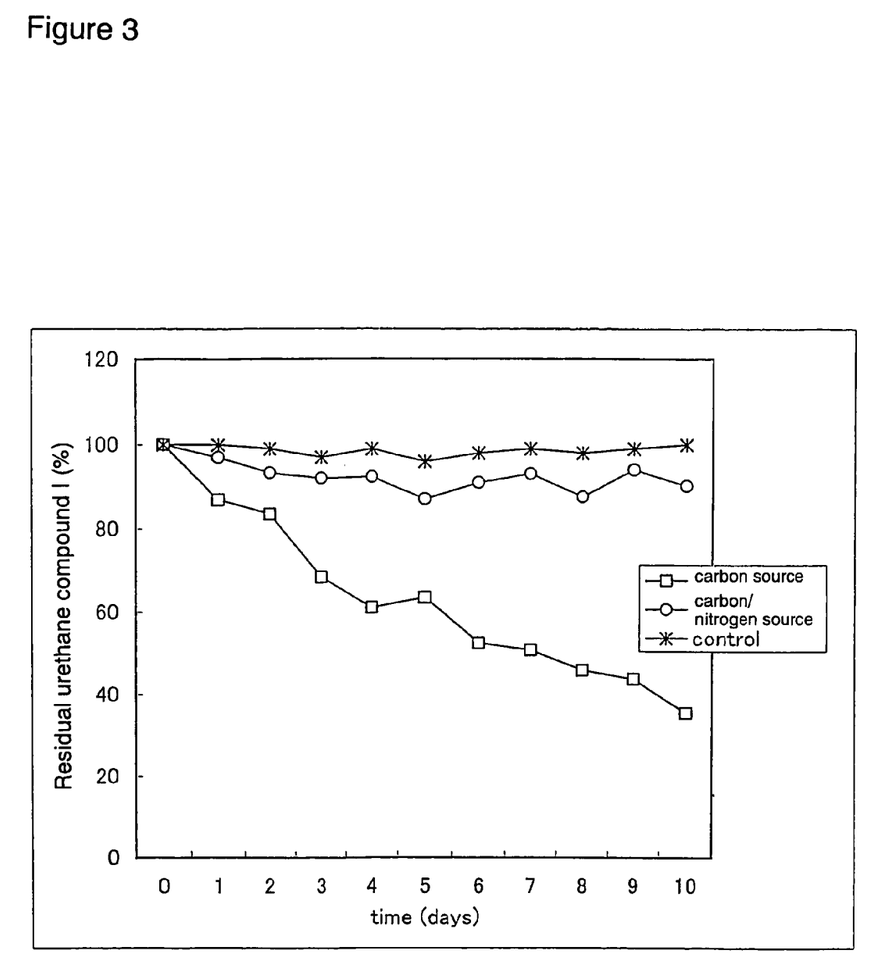
FIG. 3 shows the results measured for the amount of residual urethane compound I under each culture condition.

FIG. 3 shows the results measured for the amount of residual urethane compound I under each culture condition.

The system receiving urethane compound I as a carbon source showed about a 60% decrease in the amount of urethane compound I at 10 days after initiation of the culturing. In contrast, in the medium supplemented with urethane compound I as a carbon/nitrogen source, there was only a very small decrease in the amount of urethane compound I.

The Amount of Diamine Generated

Figure 4:
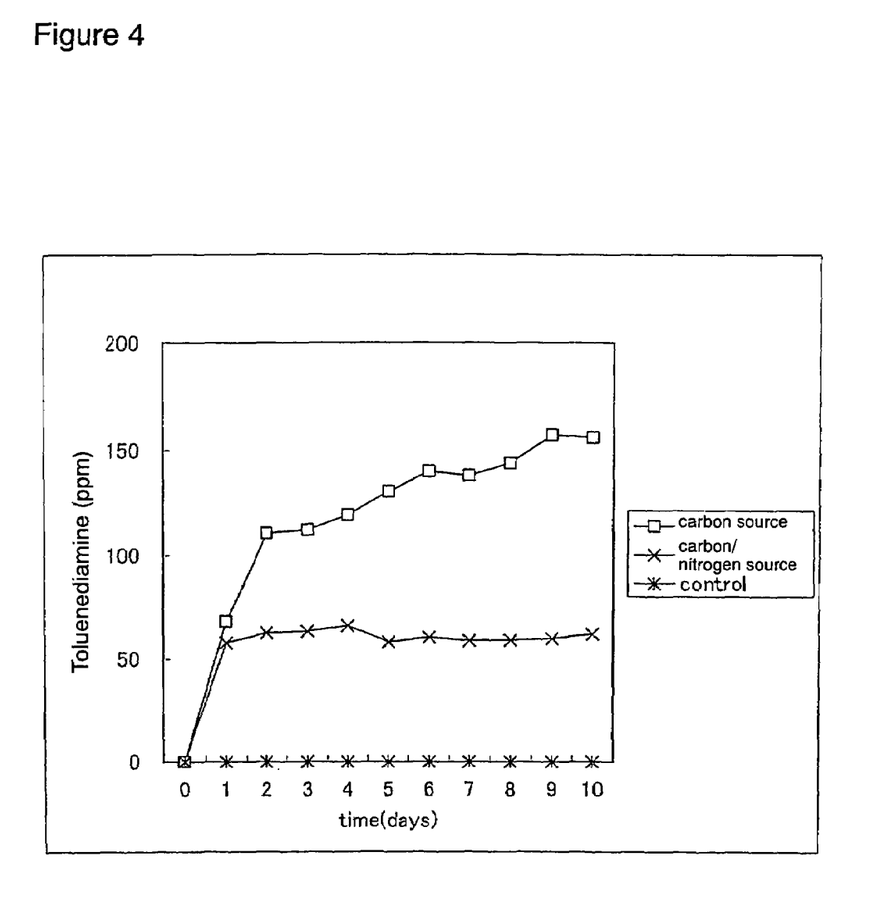
FIG. 4 shows the results measured for the amount of diamine generated under each culture condition.

FIG. 4 shows the results measured for the amount of diamine generated. The system receiving urethane compound I as a carbon source was shown to produce about 150 ppm of toluenediamine during 10 day culturing. In contrast, in the medium supplemented with urethane compound I as a carbon/nitrogen source, there was significant production of diamine at the beginning of the culturing, but followed by slight production.

The Amount of Bacterial Cells Grown

Figure 5:
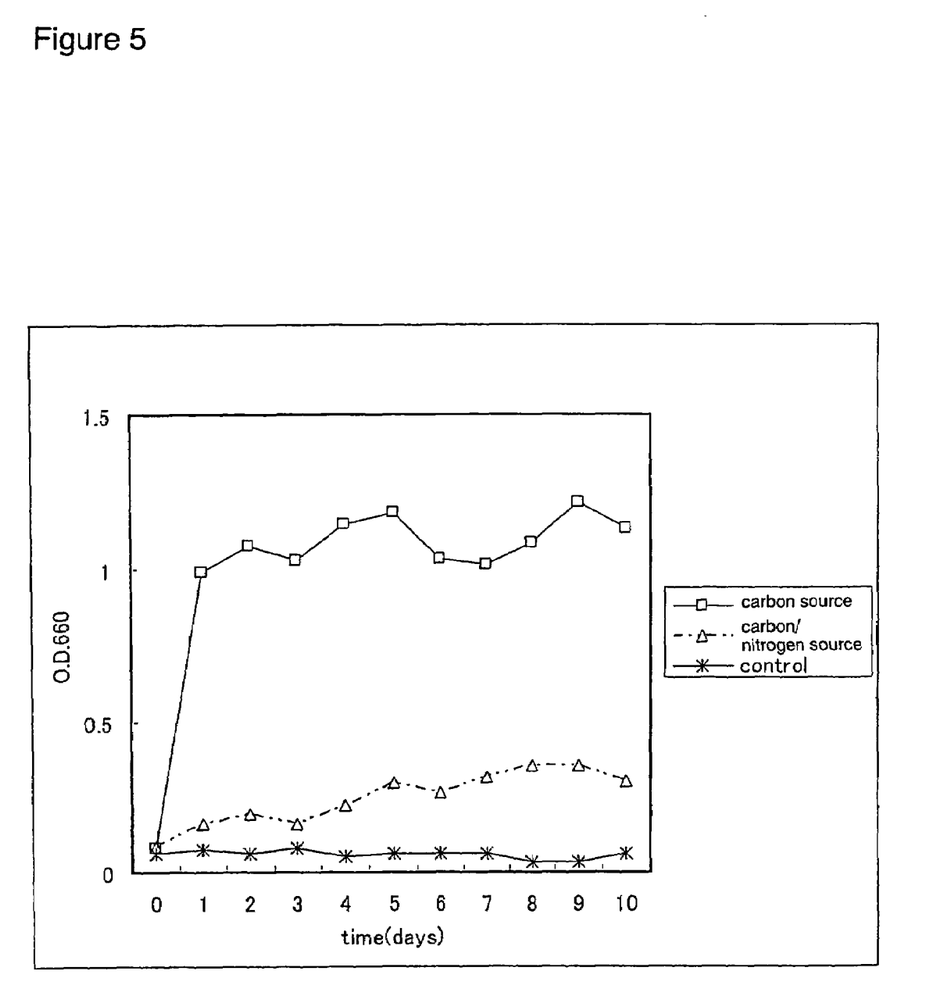
FIG. 5 shows the results measured for the amount of bacterial cells grown under each culture condition.

FIG. 5 shows the results measured for the amount of bacterial cells grown. The system receiving urethane compound I as a carbon source showed significant growth at the beginning of the culturing. In contrast, in the medium supplemented with urethane compound I as a carbon/nitrogen source, mild growth continued after day 3.

INDUSTRIAL APPLICABILITY

The strain obtained in the present invention can be expected to be adapted for various treatments of urethane compounds (particularly polyurethanes), including intensive degradation using a pure culture system of this strain, degradation in soil or compost, recycling as fertilizers, etc. Moreover, this strain is a bacterial strain and hence is advantageous for use in microbial degradation also in terms of cost because bacteria are generally easier to adapt for large scale culture than other microorganisms. The microorganism of the present invention enables complete bacterial degradation of polyurethanes when it is used in combination with bacteria capable of degrading ester bonds in urethane, e.g., *Paenibacillus amylolyticus* strain TB-13 or *Comamonas acidovorans* strain TB-35.

The invention claimed is:

1. A biologically pure culture of a microorganism belonging to the genus *Rhodococcus* and having the ability to degrade urethane bonds, or a mutant strain thereof, which has the ability to degrade urethane bonds, wherein the microorganism is *Rhodococcus equi* strain Accession No. DSM 16175.

2. The biologically pure culture according to claim 1, wherein said urethane bonds are polyurethane bonds.

* * * * *

SEQUENCE LISTING

```
<160> NUMBER OF SEQ ID NOS: 2

<210> SEQ ID NO 1
<211> LENGTH: 535
<212> TYPE: DNA
<213> ORGANISM: Rhodococcus equi TB-60

<400> SEQUENCE: 1
tagagtttga tcctggctca ggacgaacgc tggcggcgtg cttaacacat gcaagtcgag      60
cggtaaggcc cttcggggta cacgagcggc gaacgggtga gtaacacgtg ggtgatctgc     120
cctgcactct gggataagcc tgggaaactg ggtctaatac cggatatgag ctcctgtcgc     180
atggcggggg ttggaaaggt ttactggtgc aggatgggcc cgcggcctat cagcttgttg     240
gtggggtaat ggcctaccaa ggcgacgacg ggtagccggc ctgagagggc gaccggccac     300
actgggactg agacacggcc cagactccta cgggaggcag cagtggggaa tattgcacaa     360
tgggcgaaag cctgatgcag cgacgccgcg tgagggatga cggccttcgg gttgtaaacc     420
tctttcagca gggacgaagc gaaagtgacg gtacctgcag aagaagcacc ggccaactac     480
gtgccagcag cccgcggtaa tacgtagggt gcgagcgttg tccggaatta ctggg         535

<210> SEQ ID NO 2
<211> LENGTH: 497
<212> TYPE: DNA
<213> ORGANISM: Rhodococcus equi TB-60
```

```
<400> SEQUENCE: 2
ccttgtggtc ggtatacagg tggtgcatgg ctgtcgtcag ctcgtgtcgt gagatgttgg      60
gttaagtccc gcaacgagcg caaccct tgt cctgtgttgc cagcgcgtaa tggcggggac    120
tcgcaggaga ctgccggggt caactcggag gaaggtgggg acgacgtcaa gtcatcatgc    180
cccttatgtc cagggcttca cacatgctac aatggccggt acagagggct gcgataccgt    240
gaggtggagc gaatcccta aagccggtct cagttcggat cggggtctgc aactcgaccc     300
cgtgaagtcg gagtcgctag taatcgcaga tcagcaacgc tgcggtgaat acgttcccgg   360
gccttgtaca caccgcccgt cacgtcatga aagtcggtaa cacccgaagc cggtggccta   420
acccttgtgg agggagccgt cgaaggtggg atcggcgatt gggacgaagt cgtaacaagg   480
tagcctcagt cagtcaa                                                   497
```